(12) United States Patent
Biedermann et al.

(10) Patent No.: US 12,408,962 B2
(45) Date of Patent: Sep. 9, 2025

(54) BONE ANCHOR

(71) Applicant: BIEDERMANN TECHNOLOGIES GMBH & CO. KG, Donaueschingen (DE)

(72) Inventors: Timo Biedermann, Trossingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 363 days.

(21) Appl. No.: 17/495,620

(22) Filed: Oct. 6, 2021

(65) Prior Publication Data

US 2022/0096138 A1    Mar. 31, 2022

Related U.S. Application Data (63) Continuation of application No. 15/439,269, filed on Feb. 22, 2017, now Pat. No. 11,160,591.

(Continued)

(30) Foreign Application Priority Data

Feb. 25, 2016   (EP) ..................... 16157477

(51) Int. Cl.
*A61B 17/86*    (2006.01)
*A61B 17/04*    (2006.01)
(Continued)

(52) U.S. Cl.
CPC ........ *A61B 17/864* (2013.01); *A61B 17/0401* (2013.01); *A61B 17/7098* (2013.01);
(Continued)

(58) Field of Classification Search
CPC .............. A61B 17/844; A61B 17/7266; A61B 17/7258; A61B 17/7233; A61B 17/864;
(Continued)

(56) References Cited

U.S. PATENT DOCUMENTS 5,209,753 A    5/1993   Biedermann et al.
5,713,904 A *  2/1998   Errico ................ A61B 17/8605
                                                    606/327

(Continued)

FOREIGN PATENT DOCUMENTS

DE    102011017602 A1    4/2011
DE    10 2014 107 882 A1    12/2015
(Continued)

OTHER PUBLICATIONS

Extended European Search Report for Application No. 16157477.7, dated Aug. 24, 2016, 9 pages.

*Primary Examiner* — Amy R Sipp
(74) *Attorney, Agent, or Firm* — Womble Bond Dickinson (US) LLP (57) ABSTRACT

A bone anchor includes a shank having a free end, a longitudinal axis, a channel extending axially through the shank to the free end, the channel having a first width, and at least one opening extending through a wall of the shank, and a narrowing member including an elastically deformable portion configured to extend into the channel at or near the free end. The narrowing member is adjustable from a first configuration where the deformable portion defines an opening with a width smaller than the first width to restrict a substance from exiting through the free end, to a second configuration where the deformable portion is deformed radially outwardly to define an opening with a width that is at least the first width, while at least a portion of the shank (Continued)

positioned at a same axial height as the deformable portion maintains a constant outer width.

17 Claims, 5 Drawing Sheets

Related U.S. Application Data (60) Provisional application No. 62/300,031, filed on Feb. 25, 2016.

(51) Int. Cl.
  *A61B 17/70* (2006.01)
  *A61B 17/88* (2006.01)
  *A61B 17/00* (2006.01)
  *A61B 17/56* (2006.01)

(52) U.S. Cl.
  CPC ...... *A61B 17/8635* (2013.01); *A61B 17/8685* (2013.01); *A61B 17/8805* (2013.01); *A61B 17/8897* (2013.01); *A61B 2017/00862* (2013.01); *A61B 2017/564* (2013.01); *A61B 17/7035* (2013.01); *A61B 17/8605* (2013.01)

(58) Field of Classification Search
  CPC ............ A61B 17/8635; A61B 17/8685; A61B 17/7098; A61B 17/8805; A61B 17/8811; A61B 17/8816; A61B 2017/8655
  See application file for complete search history.

(56) References Cited

U.S. PATENT DOCUMENTS

| | | | |
|---|---|---|---|
| 6,994,725 B1 | 2/2006 | Goble | |
| 8,690,930 B2 | 4/2014 | Biedermann et al. | |
| 9,138,274 B1 | 9/2015 | Biesinger et al. | |
| 2003/0097132 A1* | 5/2003 | Padget | A61B 17/8685 606/65 |
| 2008/0027444 A1* | 1/2008 | Malek | A61B 17/686 606/86 A |
| 2008/0039846 A1 | 2/2008 | Lee et al. | |
| 2010/0069970 A1 | 3/2010 | Lewis et al. | |
| 2016/0113685 A1 | 4/2016 | Ishii et al. | |

FOREIGN PATENT DOCUMENTS

| | | |
|---|---|---|
| JP | H04-502567 A | 5/1992 |
| JP | 2013-509920 A | 3/2013 |
| JP | 2014-223502 A | 12/2014 |
| WO | WO 2006/108329 A1 | 10/2006 |
| WO | WO 2011/054122 A1 | 5/2011 |
| WO | WO 2012/146744 A2 | 11/2012 |

* cited by examiner

BONE ANCHOR

CROSS-REFERENCE TO RELATED APPLICATION(S)

This application is a continuation of U.S. patent application Ser. No. 15/439,269, filed Feb. 22, 2017, which claims the benefit of U.S. Provisional Patent Application Ser. No. 62/300,031, filed Feb. 25, 2016, and claims priority from European Patent Application EP 16 157 477.7, filed Feb. 25, 2016, the contents of which are hereby incorporated by reference in their entirety.

BACKGROUND

Field

The invention relates to a bone anchor having a shank with a channel extending therethrough, and a narrowing member provided in the channel at or close to one end of the channel for reducing a cross-section of the channel. The bone anchor can be used, for example, in minimally invasive surgery for the treatment of weak and/or osteoporotic bones or vertebrae.

Description of Related Art

U.S. Pat. No. 8,690,930 describes a bone anchor including a shaft having a first end and a second end, a bore extending from the first end to the second end, and a plug member which is insertable into the bore and guidable through the bore for closing the bore at the second end.

WO 2012/146744 A2 describes a bone screw with a centrally arranged opening and a plurality of openings radial thereto. Bone cement can be injected into the bone through these openings. In order to avoid cement distribution outside of the bone, a closure apparatus is proposed. In one embodiment the closure apparatus is a re-closable sleeve arranged in the bone screw and having the function of a valve. Thereby, the insertion of a closure member after having screwed the bone screw into the bone becomes unnecessary.

SUMMARY

The known bone anchors are designed to prevent escape of bone cement at the tip of the bone anchor by closing a channel of the bone anchor at the tip. For certain applications, this may be advantageous. However, for other applications, it may be not desirable or even necessary to close the channel at the tip.

Embodiments of the invention provide a bone anchor that is suitable for use in minimally invasive surgery, for example, for the treatment of osteoporotic and/or weak bones.

A narrowing member is provided in the channel that extends through the bone anchor, at or close to a free end or tip end of the bone anchor, which prevents injected bone cement from exiting through the free end. The bone anchor can be used in a minimally invasive surgical procedure, wherein the bone anchor can be guided to the implantation site by means of a guide wire, such as a Kirschner wire, that is led through the channel. Because the narrowing member reduces a cross-section of the channel without closing the channel, it is possible to pass the guide wire through the bone anchor when the narrowing member has already been placed in the channel or is already present in the channel. As a consequence, a step of closing the channel with an additional plug after placement of the bone anchor and before injecting bone cement would no longer be necessary.

The narrowing member in the channel can further permit reintroduction of the guide wire before injecting the bone cement.

After removal of the guide wire, bone cement can be injected, where the bone cement can exit through openings in the wall of the bone anchor, but is prevented from exiting through the free end.

The narrowing member may be a separate part that can be easily manufactured and then mounted to the bone anchor. By means of this, a modular system can be provided that includes a variety of shanks having, for example, different channel widths, that can be combined with suitable narrowing members that have different opening sizes which result in different narrowing effects. In this manner, a suitable bone anchor can be assembled on demand, based for example, on the viscosity of the bone cement or other substance to be injected, among other factors.

Alternatively, the narrowing member may be formed in a monolithic manner with the shank of the bone anchor. In such embodiments, the bone anchor may have less parts, but can still achieve the same functionality.

BRIEF DESCRIPTION OF THE DRAWINGS

Further features and advantages of the invention will become apparent from the description of embodiments by means of the accompanying drawings. In the drawings.

DETAILED DESCRIPTION

FIGS. 1 to 5 illustrate a first embodiment of a bone anchor. The bone anchor 1 includes a shank 2 having a free end 3, which may be shaped as a tip, and a head 4 on a side opposite to the free end 3. The head 4 has a shape of a spherical segment, and can have a recess 4a at its free end surface for engagement with a tool. A bone thread 5 is provided on at least a portion of the outer surface of the shank 2. Adjacent to the free end 3, one or more longitudinal cutting notches 5a may be provided, for example, for bone anchors with a self-cutting tip.

Figure 1:
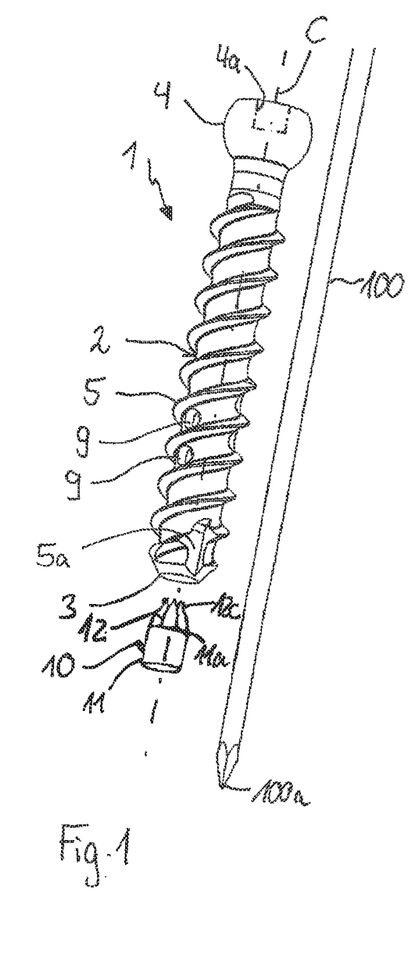
FIG. 1 shows an exploded perspective view of a first embodiment of the bone anchor, together with a guide wire.

The bone anchor 1 is cannulated, with a channel 6 extending completely through the head 4 and the shank 2, up to the free end 3. More specifically, the channel 6 may be formed by a coaxial bore having a first inner diameter and a bore axis that forms a longitudinal axis C of the channel 6 and the bone anchor 1. Adjacent to the free end 3, an accommodation space 7 for a narrowing member 10 (discussed in greater detail below) is provided that has a second inner diameter that is greater than the first inner diameter of the channel 6. Between the accommodation space 7 and the portion of the channel 6 having the first inner diameter, a shoulder 8 is formed that acts as a stop for the narrowing member 10 when the narrowing member 10 is inserted.

In a wall of the shank 2, a plurality of openings 9 is provided, where the openings 9 connect the channel 6 to the outside of the bone anchor 1. The number, size, and arrangement of the openings 9 can be designed according to the overall dimensions of the bone anchor 1, for example, for the purpose of forming outlets for bone cement and/or a pharmaceutical substance intended to be introduced into the bone anchor 1. The openings 9 may be arranged at any position. Preferably, the openings 9 are positioned in a region that is closer to the free end 3 of the shank 2 than to the head 4. Moreover, the openings 9 may be arranged between crests of the bone thread 5.

The first inner diameter of the channel 6 is sized such that a guide wire 100, such as a Kirschner wire, which is commonly used for minimally invasive surgery, can be guided through the bone anchor 1. The guide wire 100 may have a tip 100a (e.g., a tapering tip).

Figure 2:
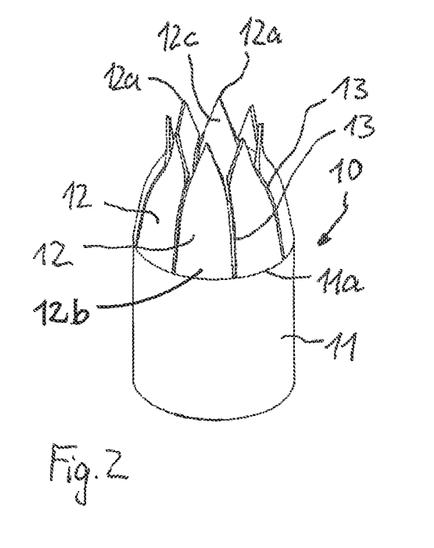
FIG. 2 shows a perspective view of the narrowing member of the bone anchor of FIG. 1.
Figure 3:
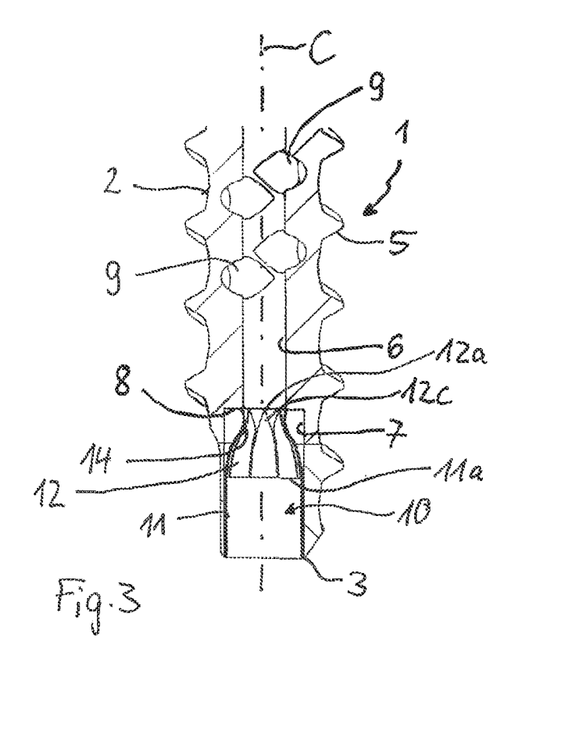
FIG. 3 shows a cross-sectional view of a lower portion of the bone anchor of FIG. 1, including the inserted narrowing member, the cross-section taken in a plane containing a longitudinal axis of the bone anchor.

As illustrated in greater detail in FIGS. 2 and 3, the narrowing member 10 is a sleeve-like piece that has a first tubular portion 11 with a maximum outer diameter that allows the sleeve-like piece to be mountable in a press-fit manner into the accommodation space 7 of the bone anchor 1. Adjacent to an edge or end 11a of the tubular portion 11, a plurality of wall portions 12 having respective free ends 12a are circumferentially arranged with their free ends 12a facing away from the tubular portion 11. Between the wall portions 12, slits 13 are provided. The wall portions 12 have a shape that may be obtained, for example, by cutting a hollow sphere-shaped or dome-shaped closed end at circumferentially equidistant sections from an outermost end point of the closed end in the direction of the edge or end 11a of the tubular portion 11. Hence, as can be seen in particular in FIG. 3, each flexible wall portion 12 has a base 12b adjacent to the edge or end 11 a of the tubular portion 11, and narrows towards a substantially triangular tip portion 12c that is adjacent to the free end 12a. The wall portions 12 are bent radially inwardly from the base 12b towards the longitudinal axis C up to a transition portion 14, where the triangular tip portion 12c starts. The triangular tip portions 12c are then bent slightly away from the longitudinal axis C. By means of this shape, the narrowing member 10 has a reduced sized opening at an end that faces away from the tubular portion 11.

The wall thickness of the wall portions 12 and the size of the slits 13 is selected such that the wall portions 12 are elastically deformable. When a radial pressure is applied from inside the narrowing member 10, the wall portions 12 are configured to move radially outwardly from resting positions with respect to the longitudinal axis C, thereby increasing a size of the opening at the transition portion 14. The wall portions 12 are configured to move back to the resting positions when the radial pressure is released, thereby narrowing the opening at the transition portion 14 again. Similarly, when a radial pressure is applied from outside on the wall portions 12, in particular on the triangular tip portions 12c, the wall portions 12 are configured to move radially inwardly from their resting positions towards the longitudinal axis C, and to move back to the resting positions when the radial pressure is released. For example, the size of the opening defined by the wall portions 12 is such that the wall portions 12 are configured to expand when a guide wire 100 or other instrument is guided through the narrowing member 10, and are configured to snap back or otherwise return to their resting positions when the guide wire 100 or other instrument is removed.

When the wall portions 12 are in their resting positions, the narrowing member 10 defines an inner diameter at least at the transition portion 14 that is smaller than the first inner diameter of the channel 6. Therefore, when the narrowing member 10 is inserted into the accommodation space 7, the opening through the bone anchor 1 is narrowed at the transition portion 14, as depicted in FIG. 3. A total axial length of the narrowing member 10 corresponds to an axial length of the accommodation space 7. The narrowing member 10 can be arranged in the accommodation space 7 in two different orientations. In FIG. 3, the narrowing member 10 is oriented in the accommodation space 7 with the triangular tip portions 12c facing towards the head 4 of the bone anchor 1. The tip portions 12c are bent slightly outwardly, to such an extent that the free ends 12a of the wall portions 12 abut against the stop provided by the shoulder 8 in this inserted configuration. In an alternative insertion configuration, the narrowing member 10 is oriented with the triangular tip portions 12c facing towards the free end 3 of the bone anchor 1.

The bone anchor 1, including the narrowing member 10, may be made from a bio-compatible material, for example, of titanium or stainless steel, of a bio-compatible alloy, such as β-titanium or NiTi-alloys, for example, Nitinol, of magnesium or magnesium alloys, or from a biocompatible plastic material, such as, for example, polyether ether ketone (PEEK) or poly-1-lactide acid (PLLA). The respective parts can be made of the same material, or can be made of different materials. In particular, the narrowing member 10 can be made of a material that exhibits high elasticity, such as Nitinol in the superelastic condition.

In the first embodiment, the narrowing member 10 is mounted to the shank 2 by press-fitting the narrowing member 10 into the accommodation space 7, such that the triangular tip portions 12c are facing towards the head 4 of the bone anchor 1. The assembly of the respective parts can take place at the manufacturer, or can be carried out directly before or during a surgery or other procedure.

Figure 4A:
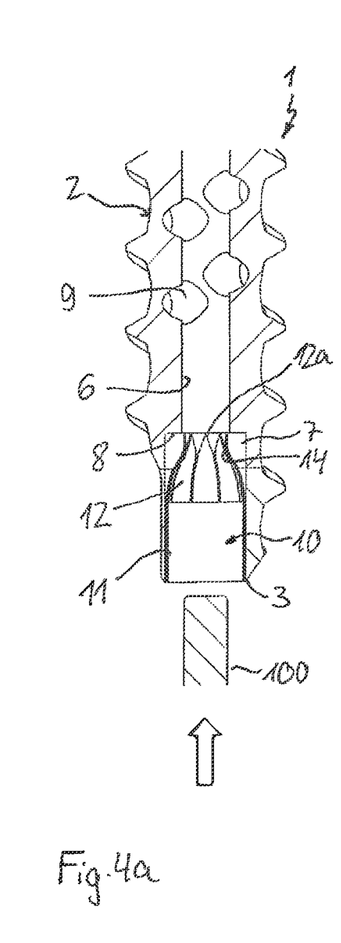
FIGS. 4a to 4e show cross-sectional views of the lower portion of the bone anchor according to FIGS. 1 to 3, during several steps of using a guide wire.
Figure 4B:
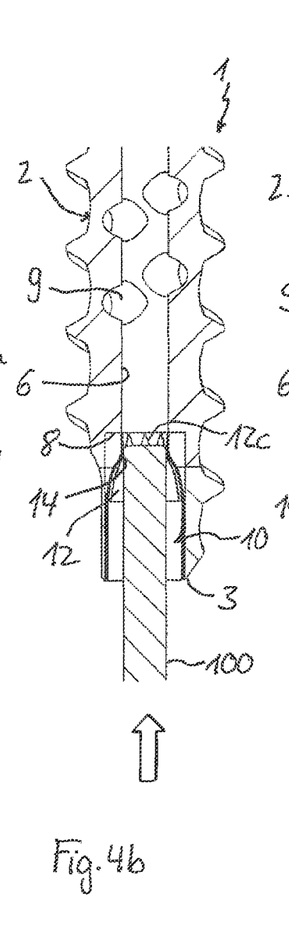
Figure 4C:
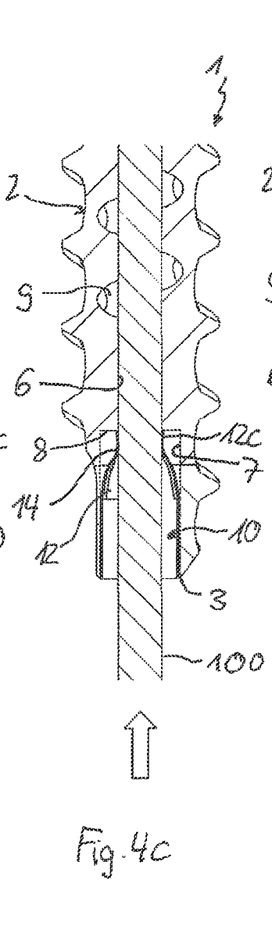
Figure 4D:
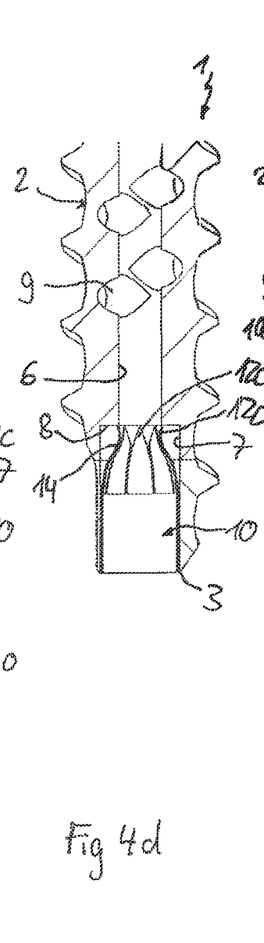

Use of the bone anchor 1 is now described with respect to FIGS. 4a to 4e. In a first step, a guide wire 100, such as a Kirschner wire, is placed or advanced percutaneously through the skin of a patient to a bone part or a vertebra of the vertebral column where the bone anchor 1 is to be finally positioned or implanted. Thereafter, as shown in FIG. 4a, the free end 3 of the bone anchor 1 with the narrowing member 10 inserted is placed onto the guide wire 100 (e.g., the guide wire 100 is inserted through the free end 3 of the bone anchor 1). As depicted in FIG. 4b, the guide wire 100 enters the narrowing member 10, is guided through the tubular portion 11, and reaches the transition portion 14 bordering the triangular tip portions 12c. An outer diameter of the guide wire 100 is greater than a resting inner diameter of the opening formed at the transition portion 14, such that the wall portions 12 are pressed slightly outwardly by the guide wire 100. As shown in FIG. 4c, the bone anchor 1 is then guided by the guide wire 100 that passes through the channel 6, and can be screwed into the corresponding bone part or the vertebra, for example, into the pedicle of the vertebra, once the bone anchor 1 reaches the intended implant site. Thereafter, as illustrated in FIG. 4d, the guide wire 100 is removed.

Figure 4E:
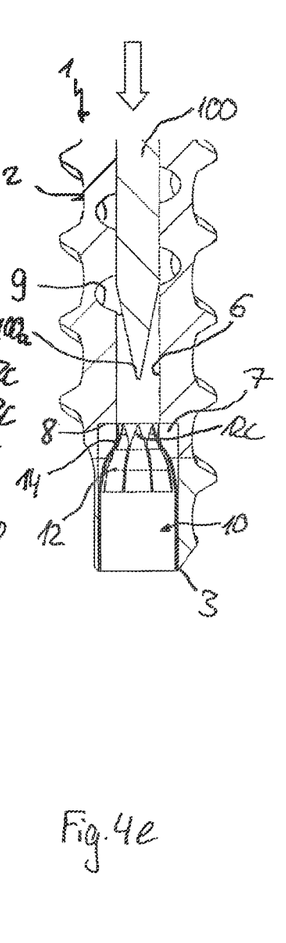

When the flexible wall portions 12 are no longer spread apart by the guide wire 100, they can return to their resting positions, where the wall portions 12 narrow the diameter of the opening through the bone anchor 1. If needed, the guide wire 100 may be re-introduced into the bone anchor 1, for example, from an end of the head 4, as shown in FIG. 4e, as long as bone cement has not yet been injected into the bone anchor 1. Since the triangular end portions 12c of the wall portions 12 are bent slightly outwardly, the tip 100a of the guide wire 100 can easily be inserted into the narrowing member 10.

Figure 5:
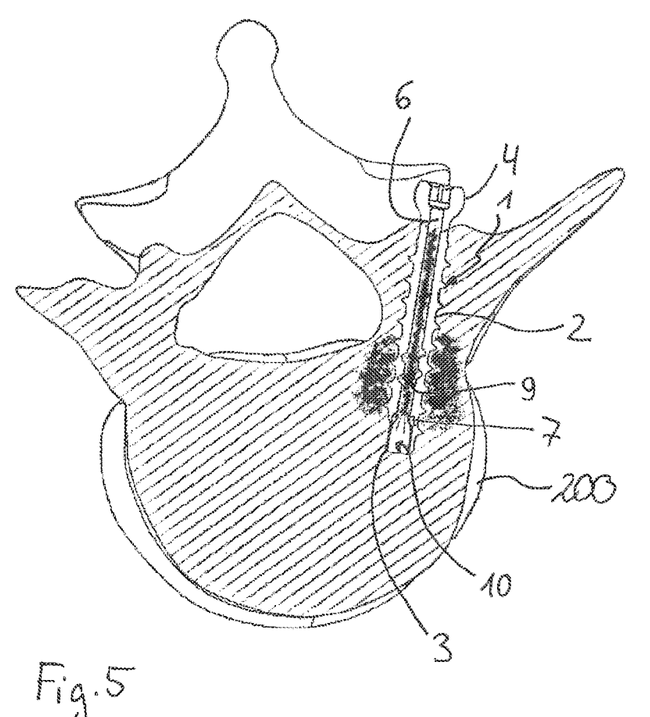
FIG. 5 shows a schematic view of a bone anchor according to the first embodiment inserted into the pedicle of a vertebra and filled with bone cement.

FIG. 5 shows the bone anchor 1 inserted into the pedicle of a vertebra 200. As shown in FIG. 5, bone cement can be injected through the head 4 into the channel 6 of the bone anchor 1. The bone cement can exit through the transverse openings 9. When the bone cement encounters or reaches the narrowing member 10, the narrow opening defined by the narrowing member 10 prevents the bone cement from exiting through the free end 3 of the bone anchor 1. A complete closure of the opening is not necessary.

In an example of stabilizing the vertebral column, at least two bone anchors 1 are implanted in adjacent vertebrae, and are connected by a stabilizing member, such as a rod. In this case, the head 4 of the bone anchor 1 can, for example, be connected to a receiving part of a polyaxial screw.

Figure 6:
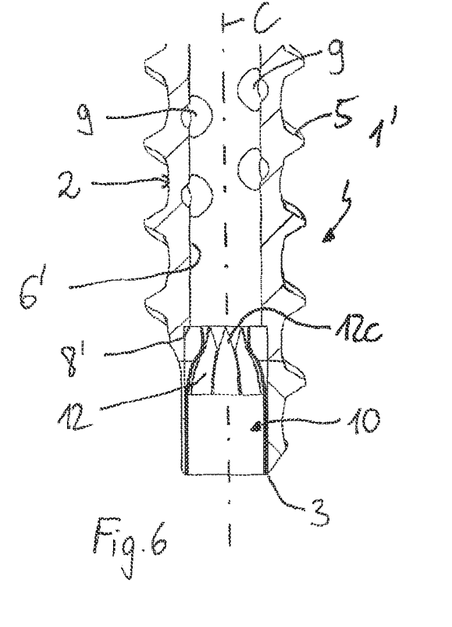
FIG. 6 shows a cross-sectional view of a lower portion of a bone anchor according to a modified first embodiment.

A modification of the first embodiment of the bone anchor is shown in FIG. 6. The bone anchor 1' has a channel 6' that has a diameter that is greater than the channel 6 of the bone anchor 1. The shoulder 8' consequently has a smaller width than the shoulder 8 of the bone anchor 1. As a result, the triangular tip portions 12c do not abut against the shoulder 8'. The narrowing member 10 in this modified embodiment can be firmly held in the accommodation space 7 by a press-fit connection, such that the narrowing member 10 cannot move further into the channel 6'.

In yet other embodiments, the inner diameters of the accommodation space 7 and of the channel 6' may also be equal.

Figure 7:
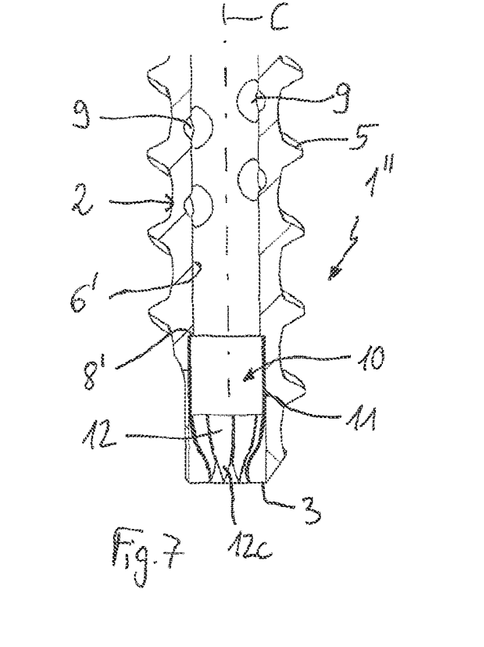
FIG. 7 shows a cross-sectional view of a lower portion of a bone anchor according to a further modified first embodiment.

A further modification of the first embodiment of the bone anchor is shown in FIG. 7. In the bone anchor 1", narrowing member 10 is mounted into the accommodation space 7 with the triangular tip portions 12c facing towards the free end 3 of the shank 2. The tubular portion 11 of the narrowing member 10 abuts against the shoulder 8', and is also firmly held in the accommodation space 7 by a press-fit connection. The narrowing of the opening through the bone anchor 1" at the free end 3 (i.e., in the region of the accommodation space 7) by the narrowing member 10 is sufficient to prevent bone cement from exiting through the free end 3. A guide wire 100 to be inserted through the bone anchor 1" can slide along the inner sides of the triangular tip portions 12c, since the tip portions 12c are bent slightly outwardly.

With the narrowing member 10 being a separate part from other portions of the bone anchor 1, 1', 1", it is possible to provide a modular system that includes a plurality of bone anchors 1, 1', 1" with channels 6, 6' having different diameters.

An appropriate bone anchor can be selected on demand before or during surgery, depending, for example, on the specific medical conditions. It is also possible to provide a plurality of narrowing members with different sizes of wall portions and different sizes of openings encompassed or defined by the wall portions. Hence, depending on several factors, such as, for example, the viscosity of the substance to be introduced and the specific medical conditions, a suitable or desired narrowing member can be assembled with a suitable or desired bone anchor.

Figure 8:
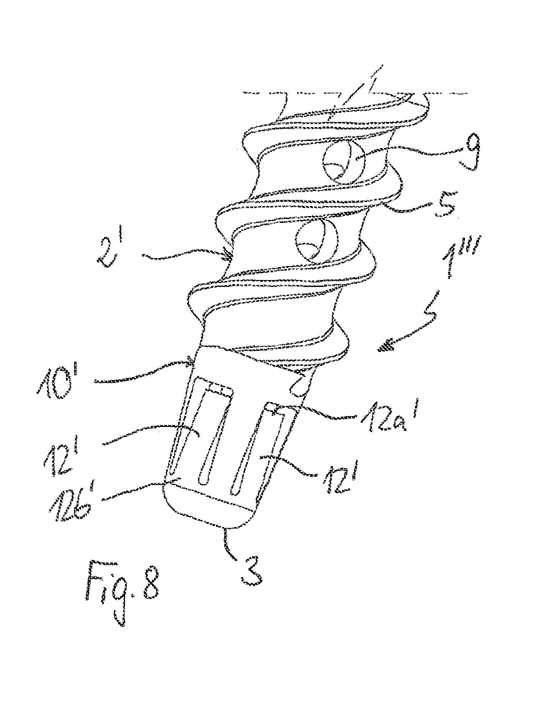
FIG. 8 shows a perspective view of a lower portion of a bone anchor according to a second embodiment.
Figure 9:
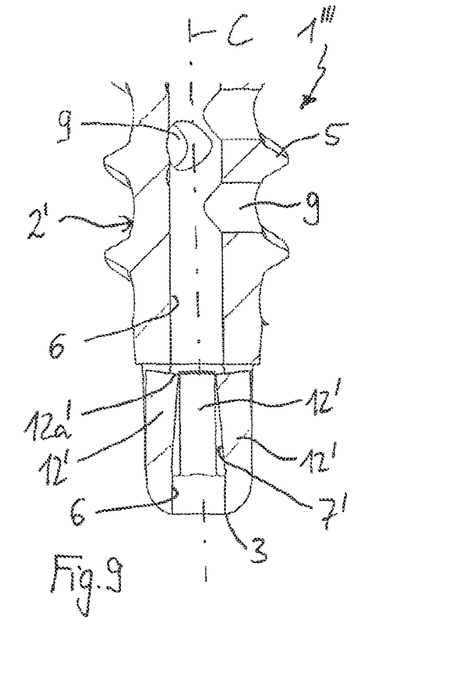
FIG. 9 shows a cross-sectional view of the lower portion of the bone anchor of FIG. 8, the cross-section taken in a plane containing a longitudinal axis of the bone anchor.

A second embodiment of the bone anchor is shown in FIGS. 8 and 9. For the bone anchor 1'", narrowing member 10' is formed monolithically with shank 2'. To accomplish this, the narrowing member 10' forms an end portion of the shank 2'. The channel 6 may extend entirely through the bone anchor 1'" to the free end 3 with a same inner diameter, where an end section of the channel 6 forms an accommodation space 7' for the narrowing member 10'. In a wall of the narrowing portion 10', a plurality of circumferentially arranged flexible wall portions 12' are provided, made for example by cutting the wall of the narrowing portion 10', such that the free ends 12a' of the wall portions 12' face towards the head 4, and the bases 12b' of the wall portions 12' are connected to the shank 2'. The flexible wall portions 12' are bent slightly inwards towards the longitudinal axis C, thereby forming the narrowing member 10' that narrows the opening through the bone anchor 1'". A guide wire (not shown) may be guided from the free end 3 through the channel 6, thereby pressing the flexible wall portions 12' slightly outwardly. When the guide wire is removed, the flexible wall portions 12' return back to their resting positions, narrowing the opening once again. Also in this embodiment, bone cement can be prevented from exiting through the free end 3.

Figure 10:
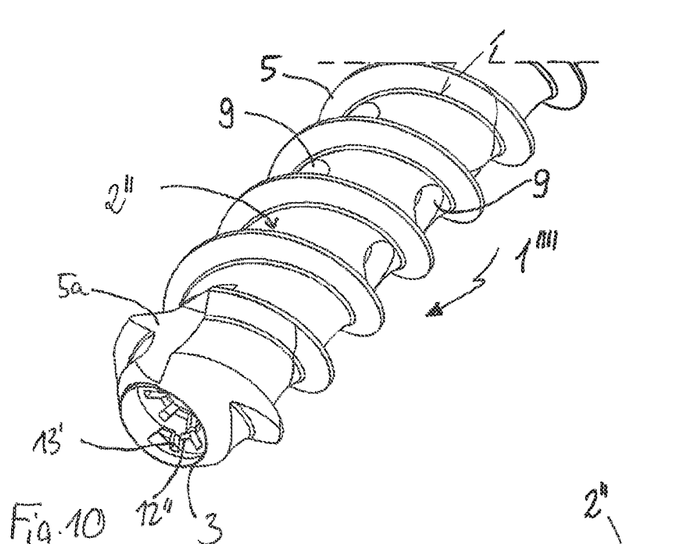
FIG. 10 shows a perspective view of a lower portion of a bone anchor according to a third embodiment.
Figure 11:
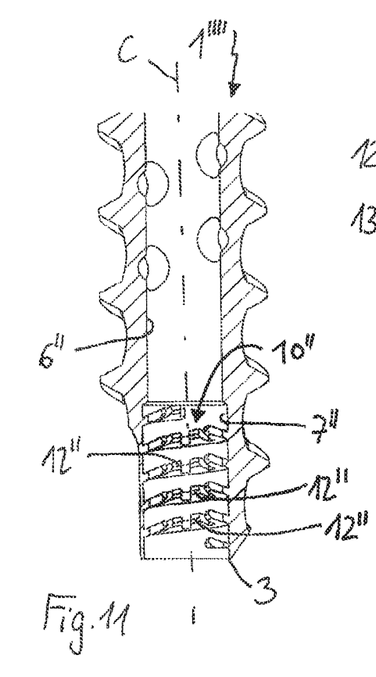
FIG. 11 shows a cross-sectional view of the lower portion of the bone anchor of FIG. 10, the cross-section taken in a plane containing a longitudinal axis of the bone anchor.
Figure 12:
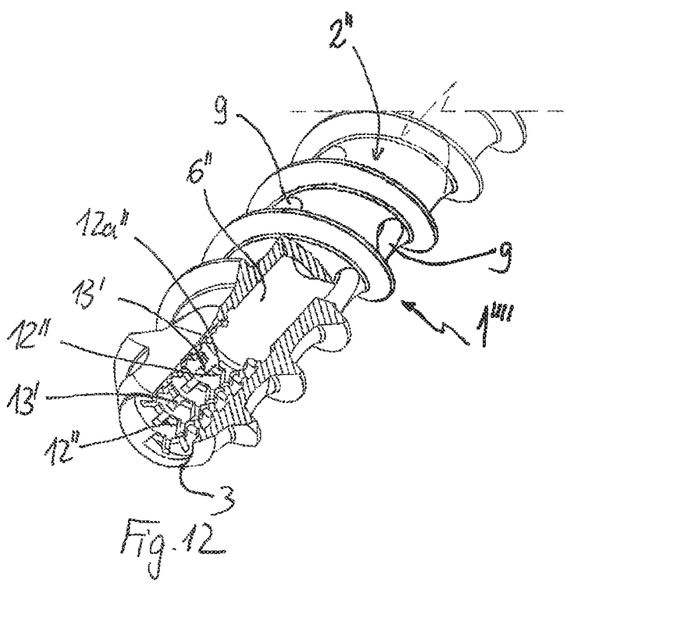
FIG. 12 shows a perspective view of the bone anchor of FIGS. 10 and 11, with a portion shown in partial cross-section.

A third embodiment of the bone anchor is shown in FIGS. 10 to 12. For the bone anchor 1"", narrowing member 10" is also formed in a monolithic manner with shank 2". The accommodation space 7" has a slightly larger inner diameter than the inner diameter of the channel 6" in the main part of the shank 2". At an inner wall of the accommodation space 7" in a region adjacent to the free end 3, a thread is formed. The upper flank of the thread faces or is directed towards the head 4, forming an undercut (i.e., the thread has a negative flank angle). A plurality of coaxial slots 13' are provided in the crests of the thread, such that flexible wall portions 12" are formed. By means of the negative flank angle, the free ends 12a" of the flexible wall portions 12" face or are directed towards the head 4. The flexible wall portions 12" narrow the channel 6" in the region adjacent to the free end 3. In this manner, bone cement can be prevented from exiting through the free end 3. The bone anchor 1" can preferably be made, for example, by an additive manufacturing method, such as laser-sintering or laser-melting. This method allows production of the internal flexible wall portions 12" monolithically with the shank 2" in a simple and fast manner.

Meanwhile, the specific shape of the narrowing member 10" is only an example, and various other shapes can also be contemplated.

In addition, further modifications of the above-described embodiments are also possible. For example, the head 4 can have any other shape, or the bone anchor may be a headless bone anchor. In some embodiments, the bone anchor can be connected to a receiving part to form, for example, a monoaxial or a polyaxial bone screw.

When the narrowing member is a separate part, the narrowing member can be connected to the shank in ways other than a press-fit connection. For example, the narrowing member can be connected to the shank via, for example but not limited to, a threaded connection.

Meanwhile, while the bone engagement structure of the embodiments shown is a bone thread, other bone engagement structures can instead be provided, such as barbs, or in some embodiments, the bone engagement structure can be omitted, so that the bone anchor is a bone nail.

The number of openings and the sizes and shapes of the openings may also vary. In some embodiments, at least one opening may be sufficient. In some embodiments, the channel may have a cross-section that varies along a length of the channel.

In other embodiments, substances other than bone cement, such as pharmaceutical substances, may also be injected into the bone anchor. The narrowing member can be selected with a specific opening, for example, depending on a viscosity of the substance to be injected.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchor comprising:
   a shank having a distal free end that forms a closed ring, a longitudinal axis, a channel extending axially through the shank to the free end, and at least one opening extending transversely to the longitudinal axis through a wall of the shank to connect the channel with an outside of the bone anchor; and
   wherein a narrowing member formed monolithically with the shank comprises a plurality of flexible portions at or near the free end of the shank that are formed at least partially by a plurality of slots that extend into an inner wall of the shank and that extend substantially parallel to the longitudinal axis, wherein each flexible portion of the plurality of flexible portions extends axially from a first end that is closer to the free end of the shank to an opposite proximal most free end that faces away from the free end of the shank, and wherein at least part of each flexible portion of the plurality of flexible portions protrudes into the channel with a portion extending closest radially to the longitudinal axis being closer axially to the free end of the flexible portion than to the first end of the flexible portion.

2. The bone anchor of claim 1, wherein the narrowing member is at least partially elastically deformable in a radially outwardly direction.

3. The bone anchor of claim 1, wherein the plurality of flexible portions comprise a plurality of wall portions.

4. The bone anchor of claim 1, wherein the plurality of flexible portions are formed as protruding wall portions at the inner wall of the shank.

5. The bone anchor of claim 3, wherein at least two of the plurality of slots are connected by a circumferentially extending slot to form at least one of the plurality of wall portions.

6. The bone anchor of claim 1, wherein the narrowing member is configured to permit passing of a guide wire or other instrument therethrough.

7. The bone anchor of claim 6, wherein the narrowing member is configured to be deformed radially outwardly when the guide wire or the other instrument extends therethrough, and is configured to move back towards a non-deformed configuration when the guide wire or the other instrument is removed.

8. The bone anchor of claim 1, wherein the plurality of flexible portions are formed by a projection that extends circumferentially around the inner wall of the shank and that is divided into segments by the plurality of slots, with each of the segments forming one of the plurality of flexible portions.

9. The bone anchor of claim 1, wherein a first section of the channel that is positioned farther from the free end of the shank has a first width and a second section of the channel that is positioned closer to the free end of the shank has a width that is greater than the first width, and wherein the narrowing member comprising the plurality of flexible portions is formed at the second section of the channel.

10. The bone anchor of claim 9, wherein the narrowing member is at least partially elastically deformable in a radially outwardly direction.

11. The bone anchor of claim 9, wherein the plurality of flexible portions are formed as a plurality of protruding wall portions at an inner wall of the shank that protrude into the channel.

12. The bone anchor of claim 11, wherein the plurality of protruding wall portions are arranged in a thread-like manner.

13. The bone anchor of claim 11, wherein adjacent protruding wall portions from among the plurality of protruding wall portions are separated circumferentially from one another by corresponding ones of the plurality of slots.

14. A bone anchor comprising:
    a shank having a distal free end that forms a closed ring, a longitudinal axis, a channel extending axially through the shank to the free end, and at least one opening extending transversely to the longitudinal axis through a wall of the shank to connect the channel with an outside of the bone anchor; and
    wherein a narrowing member formed monolithically with the shank comprises a plurality of flexible portions at or near the free end of the shank, wherein each flexible portion of the plurality of flexible portions extends axially from a first end that is closer to the free end of the shank to an opposite proximal most free end that faces away from the free end of the shank, wherein at least part of each flexible portion of the plurality of flexible portions protrudes into the channel with a portion extending closest radially to the longitudinal axis being closer axially to the free end of the flexible portion than to the first end of the flexible portion, and wherein each flexible portion of the plurality of flexible portions is configured to flex at least partially radially outwardly relative to the longitudinal axis from a first position to a second position, and to move from the second position back towards the first position.

15. The bone anchor of claim 14, wherein the narrowing member is at least partially elastically deformable.

16. The bone anchor of claim 14, wherein the plurality of flexible portions comprise a plurality of wall portions.

17. The bone anchor of claim 14, wherein the plurality of flexible portions are formed as protruding wall portions at an inner wall of the shank.

* * * * *